United States Patent [19]

Sternheimer

[11] 3,961,039
[45] June 1, 1976

[54] URINARY SEDIMENT STAIN

[76] Inventor: Richard Sternheimer, 1765 East 55th St., Chicago, Ill. 60615

[22] Filed: Apr. 24, 1975

[21] Appl. No.: 571,067

Related U.S. Application Data

[63] Continuation-in-part of Ser. No. 410,917, Oct. 29, 1973, abandoned.

[52] U.S. Cl. .................................... 424/3; 8/1 XA; 8/3; 8/25; 424/7; 424/8
[51] Int. Cl.$^2$ ..................... G01N 1/30; G01N 33/16
[58] Field of Search ................ 424/3, 7, 8; 8/1 XA, 8/3, 94 R, 25

[56] References Cited
UNITED STATES PATENTS

OTHER PUBLICATIONS

Gray, The Ency. of Micro. & Microtech. VanNostraud Reinhold Co. N.Y. 1973 (recd Lib. of Congress 10/3/73 pp. 471, 472, 475–477, 479, 549–550.
Chem. Abs. vol. 50, 1956, pp. 15832c.
Chem. Abs. vol. 64, 1966, pp. 20184bc.
Gurr, Synthetic Dyes in Biol. Med. & Chem., Acd. Press, N.Y. 1971 pp. 64–65, 114–116, 140–142.
Scott, Nature, vol. 209, 1966 pp. 985–987.
Conn. Biol. Stains, Biotech. Pub. Geneva, N.Y. 1946 pp. 136–138, 149–153, 251, 255.
Sternheimer & Malbin, Amer. J Med. vol. 11, 1951 pp. 312–323.

*Primary Examiner*—Albert T. Meyers
*Assistant Examiner*—A. P. Fagelson
*Attorney, Agent, or Firm*—Prangley, Dithmar, Vogel, Sandler & Stotland

[57] ABSTRACT

A stain for unfixed, wet urinary sediment and cellular elements of serous effusions comprising in combination a preferential nucleus-seeking dye and a preferential cytoplasm-seeking dye providing a readily detectable difference between nuclear cellular material and cytoplasmic cellular material while at the same time prominently staining urinary casts, other mucoid material and bacterial elements.

5 Claims, No Drawings

URINARY SEDIMENT STAIN

This application is a continuation-in-part of application Ser. No. 410,917, filed Oct. 29, 1973, now abandoned.

This invention relates to a stain for unfixed, wet urinary sediments and cellular elements of serous effusions and, more particularly, to a stain which prominently stains urinary casts and other mucoid material.

It is a principal object of the present invention to provide a stain and a method for staining unfixed, wet urinary sediment and cellular elements of serous effusions comprising in combination a preferential nucleus-seeking dye, and a preferential cytoplasmic-seeking dye, the combined dyes having a pH of from about 2 to about 5, whereby the preferential nucleus-seeking dye stains the nucleus of damaged cells present in the sediment or serous effusions a first color and the preferential cytoplasm-seeking dye stains the cytoplasm of the cells present in the sediment or serous effusions a second color and the mucoproteins present in the sediment or serous effusions are distinctly stained to permit differentiation between cellular nuclear material and cellular cytoplasmic material and mucoprotein material.

Another object of the present invention is to provide a stain and method of the type set forth wherein the nucleus-seeking dye is a copper phthalocyanin dye.

Still another object of the present invention is to provide a stain and method of the type set forth wherein the cytoplasm-seeking dye is a red xanthene dye.

Staining of wet, unfixed cells and formed elements in urine, sputum or serous effusions for the purpose of morphological recognition and identification has been considered to be of limited value. The exfoliated cells, suspended for an undetermined period of time in a medium of altered osmolarity, present variable degrees of viability, hydration, density and permeability. This, in turn, affects their transparency in ordinary light microscopy and the uptake of dyes as well. In hydrated cells, the initial, predominantly electrostatic binding of basic dyes by nucleic acid phosphate groups is rendered difficult by competing basic groups of loosely associated proteins. To overcome this competition and to achieve staining, especially of the nucleus, relatively high, frequently toxic dye concentrations are required which ultimately result in killing of the cell.

This differs from conventional fixation methods, where the cell is first killed by inducing dehydration, coagulation, and denaturation of proteins, a process believed to result in a loosening of the competing protein bindings, thereby enhancing the capacity of the dyes, and in the stabilization of cell structures which permits better recognition of structural detail.

There would, therefore, seem to be no advantage in using wet stain methods, except that they increase the visibility of cells presenting variable states of functional alterations. More important, however, is the fact that with the higher dye concentrations used, the cells stain so rapidly that a direct microscopic observation of cell reaction to the staining procedure becomes possible. Since the majority of the dyes are toxic to living cells, the cellular response to this injurious effect, ranging from variable staining affinities to actual structural alterations is likely to be an indication of the "vitality" or the defensive strength of the cells and thereby also of the degree of damage, the cells may have suffered before the observation started. Thus, a dynamic element, namely the relationship between an induced graded injury to the cells and their ensuing functions and morphological alterations can simultaneously be investigated. It is true, that for this type of observation, more refined, quantitating and less damaging procedures, like phase-contrast, interference and flourescence microscopy have come into increasing use, but they do not supersede supravital staining for the purpose of morphological identification and observation.

As a background to the present invention, a Dr. Malbin and I in 1951 disclosed a two-part stain useful in analyzing wet urine sediment. That stain has been produced for years and sold commercially as the Sternheimer-Malbin stain, the initial report of the stain appearing in the American Journal of Medicine, Vol. 11, No. 3, pages 312 to 323 (September, 1951). The Sternheimer-Malbin stain consists of two solutions wherein solution A consists of;

1. Methylrosaniline chloride (crystal violet) — 3.0 Gm.
2. Ethyl alcohol 95%—20.0 ml.
3. Ammonium exalate 0.8 Gm. and distilled pure water to 80 ml.

and solution B consists of;

1. Safranine 0—0.25 Gm.
2. Ethyl alcohol 95%—10.0 ml.
3. Distilled water to 100 ml.

Three parts of solution A are mixed with 97 parts of solution B and filtered. The combined solution is stable for a period of about three months, whereas the individual solutions are stable indefinitely. It is suggested that the combined solutions be filtered every two weeks. The technique of using the Sternheimer-Malbin stain is well known in the medical field and is also disclosed in detail in an illustrated booklet reprinted by Abbott Laboratory from "WHATS NEW", No. 218, Summer 1960. Since the Sternheimer-Malbin stain, however, contains 10% alcohol, which by its dehydrating and toxic effects shrinks the cells, renders details less visible and alters dye uptake, many of the advantages of supravital staining are lost.

The stain of the present invention is a non-alcoholic supravital stain in contradistinction to the Sternheimer-Malbin stain. Furthermore, the stain of the present invention renders hyaline casts and other mucoproteinaceous material distinct to enable the viewer to identify these materials. The clear delineation of the form of casts, achieved by the dye, permits with a great degree of precision to differentiate casts which are formed in the diseased kidney and then excreted from other mucoid materials likely to be a product of the lower urinary tract (pseudocasts, cylindroids, mucous threads). An additional feature of my new stain is that it enhances the contrast between cellular nuclear material and cellular cytoplasmic material and permits the viewing of the cells in the agonal state to provide further information. In particular, it facilitates recognition and differentiation of lencocytes from lymphocytes, monocytes and renal tubular cells.

As is well known in the field, many dyes used in stains are proprietary items wherein the exact chemical formula is not known. Nevertheless, those skilled in the art recognize the various alternatives for the dyes and it is intended in the hereinafter appended description to include the well known alternatives for specific dyes where only a specific dye is mentioned. For instance, the mention of National Fast Blue clearly is intended to include Alcian Blue, Astrablau as well as the related Alcian Green and Alcian Yellow dyes. While it is true that some of these dyes will work better than others, it is well within the skill of the artisan to substitute one for the other to determine the specific dye which gives the greatest contrast.

EXAMPLE I

A two-part stain was provided wherein 4 parts of a 2% by weight National Fast Blue solution was mixed with 3 parts of a 2% by weight Pyronin B solution. The pH of the combined stain was 3.5. By a capillary pipette, 1 drop was added to 2 drops of urine sediment spun down from a freshly voided specimen and thoroughly mixed. One drop of the sediment dye mixture was placed on a glass slide, covered with a coverglass and microscopically examined.

The extent of damage to the cell determines which dye the nucleus of the cell accepts. Damaged cellular material will stain blue in the nuclear material and red in the cytoplasmic material, while relatively undamaged cells remain unstained at first or will stain red in both the nuclear material and the cytoplasmic material. Mucoproteins such as hyaline casts stain blue and are readily discernable from the nuclear cellular material because of their different density, transparency and their shape.

The above example shows that the use of the combination stain permits visualizing nuclear and cytoplasmic structures in contrasting colors, thereby permitting differentiation of the cellular elements. Hyaline casts which are difficult to view in light microscopy due to the little difference in the refractive index of the cast and the urine are brought into striking prominence and therefore cellular inclusions inside the cast can be recognized and their nature determined. Finally, the use of the combination stain permits observations of the changes in the surviving cells in their agonal state wherein the nuclear material changes in color from red to blue thereby permitting conclusions as to their functional state. This is a distinct advantage over the staining of the fixed cells which induces cell death prior to the staining of the cell.

It has also been found that the amount of dye taken up by the cells is an indication of their functional integrity. In a given suspending solution, the same dye concentration will stain fresh cells not at all or very slowly, while more damaged cells will show red staining, both of cytoplasm and nucleus, and severely altered cells or dead cells show blue nuclear staining immediately. This is especially evident in the staining of polymorphonuclear leucocytes. It is seen, therefore, that the investigator will be able to differentiate between slightly damaged and severely damaged cells by the respective amount and type of dye taken up.

It is known that dye such as Pyronin B will stain both nuclear material and cytoplasmic material at low pH's when used alone but when combined with a certain basic dye like Methyl Green will preferentially stain cytoplasmic material. When used in the combination set forth above and the following examples, the Pyronin B shows a remarkable degree of selectivity or preference for RNA-rich structures such as present in the cytoplasm, whereas the National Fast Blue shows a remarkable selectivity or preference for DNA-rich structures such as the nucleus and in addition also to mucoproteins. It is hereinafter understood that the use of the term "preferential nucleus-seeking dye" includes dyes which when used in the combinations set forth herein will preferentially seek out and stain the nucleus. Similarly, the use of the term "preferential cytoplasmic-seeking dye" includes dyes which when used in the combinations set forth herein will seek out and preferentially stain the cytoplasmic material, taking into account the effect of cell damage on the dying of the nuclear material.

The pH of the dyes used in the following examples varied somewhat, but in general, the pH of the National Fast Blue was about 2.4, the pH of the Alcian Blue was about 3.9, the pH of the Astrablau was about 4.8 and the pH of the Pyronin B was from about 2.0 to about 2.7. The various dye mixtures of National Fast Blue, or Alcian Blue or Astrablau and Pyronin B had a pH of from about 2.1 to about 4.5 depending upon the particular dyes mixed. In any event, since about 1 drop of the dye mixture was added to 2 drops of the urine sediment, the resulting mixture had a higher pH because the pH of urine usually varied from about 5 to about 6.

The pH values of the dye mixtures and of the dye and urine mixtures determines what material is dyed, since copper phthalocyanin dyes such as National Fast Blue are almost specific for mucopolysaccharides at pH's of from about 2 to about 2.4. At higher pH's the copper phthalocyanin dyes stain not only the mucopolysaccharides but also the nuclear material, but show no affinity for cytoplasmic material. Pyronin B used alone at low pH's will stain both nuclear and cytoplasmic material but when Pyronin B is combined with a basic dye such as National Fast Blue, the Pyronin preferentially will stain the cytoplasmic material.

The National Fast Blue dye used in this example is a copper phthalein dye. Alternatives for the National Fast Blue include Alcian Blue, Astrablau, Alcian Green and Alcian Yellow which is not a copper phthalein dye. The Pyronin B is a red xanthene dye and alternatives for the Pyronin B are Pyronin Y, Rhodamine 6G and Acridine red.

EXAMPLE II

EXAMPLE I was repeated using a combination of 4 parts of a 2% by weight National Fast Blue solution and 4 parts of a 2% by weight Pyronin B solution. The pH of the combined stain was 2.9 and 1 drop of the above stain was mixed with 2 drops of urine and thereafter subjected to microscopic examination. All of the various constitutents of the urine specimen set forth above were visible with the casts being distinct from the cellular material and the nuclear material being distinct from the cytoplasmic material.

EXAMPLE III

EXAMPLE I was repeated using a combination of 4 parts of a 2% by weight National Fast Blue solution and 5 parts of a 2% by weight Pyronin B solution. The pH of the combined stain was 2.75 and one drop of the above stain was mixed with 2 drops of urine and thereafter subjected to microscopic examination. All of the various constituents of the urine specimen set forth above were visible with the casts being distinct from the cellular material and the nuclear material being distinct from the cytoplasmic material.

EXAMPLE IV

EXAMPLE I was repeated using a combination of 4 parts of a 2% by weight National Fast Blue solution and 6 parts of a 2% by weight Pyronin B solution. The pH of the combined stain was 2.55 and 1 drop of the above stain was mixed with 2 drops of urine and thereafter subjected to microscopic examination. All of the various constituents of the urine specimens set forth above were visible with the casts being distinct from the cellular material and the nuclear material being distinct from the cytoplasmic material.

EXAMPLE V

EXAMPLE I was repeated using a combination of 4 parts of a 2% by weight Alcian Blue 8GX solution and 3 parts of a 2% by weight Pyronin B solution. The pH of the combined stain was 3.5 and 1 drop of the above stain was mixed with 2 drops of urine and thereafter subjected to microscopic examination. All of the various constituents of the urine specimen set forth above were visible with the casts being distinct from the cellular material and the nuclear material being distinct from the cytoplasmic material.

EXAMPLE VI

EXAMPLE I was repeated using a combination of 4 parts of a 2% by weight Alcian Blue 8GX solution and .4 parts of a 2% by weight Pyronin solution. The pH of the combined stained was 3.3 and 1 drop of the above stain was mixed with 2 drops of urine and thereafter subjected to microscopic examination. All of the various constituents of the urine specimen set forth above were visible with the casts being distinct from the cellular material and the nuclear material being distinct from the cytoplasmic material.

EXAMPLE VII

EXAMPLE I was repeated using a combination of 4 parts of a 2% by weight Alcian Blue 8GX solution and 6 parts of a 2% by weight Pyronin solution. The pH of the combined stain was 3.2 and 1 drop of the above stain was mixed with 2 drops of urine and thereafter subjected to microscopic examination. All of the various constituents of the urine specimen set forth above were visible with the casts being distinct from the cellular material and the nuclear material being distinct from the cytoplasmic material.

EXAMPLE VIII

EXAMPLE I was repeated using a combination of 4 parts of a 2% by weight Astrablau solution and 3 parts of a 2% by weight Pyronin solution. The pH of the combined stain was 4.7 and 1 drop of the above stain was mixed with 2 drops of urine and thereafter subjected to microscopic examination. All of the various constituents of the urine specimen set forth above were visible with the casts being distinct from the cellular material and the nuclear material being distinct from the cytoplasmic material.

EXAMPLE IX

EXAMPLE I was repeated using a combination of 4 parts of a 2% by weight Astrablau solution and 4 parts of a 2% by weight Pyronin solution. The pH of the combined stain was 4.45 and 1 drop of the above stain was mixed with 2 drops of urine and thereafter subjected to microscopic examination. All of the various constituents of the urine specimen set forth above were visible with the casts being distinct from the cellular material and the nuclear material being distinct from the cytoplasmic material.

EXAMPLE X

EXAMPLE I was repeated using a combination of 1 part of a 2% by weight National Fast Blue solution and 2 parts of a 1.3% by weight solution of Rhodamine 6G. The pH of the combined stain was 2.3 and one drop of the above stain was mixed with 2 drops of urine and thereafter subjected to microscopic examination. All of the various constituents of the urine specimen set forth above were visible with the casts being distinct from the cellular material and the nuclear material being distinct from the cytoplasmic material.

EXAMPLE XI

EXAMPLE I was repeated using a combination of 1 part of a 2% by weight National Fast Blue solution and 1 part of a 0.8% by weight Acridine Red solution. The pH of the combined stain was 2.8 and 1 drop of the above stain was mixed with 2 drops of urine and thereafter subjected to microscopic examination. All of the various constituents of the urine specimen set forth above were visible with the casts being distinct from the cellular material and the nuclear material being distinct from the cytoplasmic material.

EXAMPLE XII

EXAMPLE I was repeated using a combination of 5 parts of a 2% by weight Astrablau solution and 1 part of a 2% by weight Pyronin solution. The pH of the combined stain was about 5 and one drop of the above stain was mixed with two drops of urine and thereafter subjected to microscopic examination. All of the various constituents of the urine specimen set forth above were visible with the casts being distinct from the cellular material and the nuclear material being distinct from the cytoplasmic material.

EXAMPLE XIII

EXAMPLE I was repeated using a combination of 4 parts of a 2% by weight Astrablau solution and 1 part of a 2% by weight Pyronin solution. The pH of the combined stain was slightly less than about 5 and one drop of the above stain was mixed with two drops of urine and thereafter subjected to microscopic examination. All of the various constituents of the urine specimen set forth above were visible with the casts being distinct from the cellular material and the nuclear material being distinct from the cytoplasmic material.

EXAMPLE XIV

EXAMPLE I was repeated using a combination of 3 parts of a 2% by weight Astrablau solution and 1 part of a 2% by weight Pyronin solution. The pH of the combined stain was about 4 and one drop of the above stain was mixed with two drops of urine and thereafter subjected to microscopic examination. All of the various constituents of the urine specimen set forth above were visible with the casts being distinct from the cellular material and the nuclear material being distinct from the cytoplasmic material.

EXAMPLE XV

EXAMPLE I was repeated using a combination of 2 parts of a 2% by weight Astrablau solution and 1 part of a 2% by weight Pyronin solution. The pH of the combined stain was slightly less than about 4 and one drop of the above stain was mixed with two drops of urine and thereafter subjected to microscopic examination.

All of the various constituents of the urine specimen set forth above were visible with the casts being distinct from the cellular material and the nuclear material being distinct from the cytoplasmic material.

EXAMPLE XVI

EXAMPLE I was repeated using a combination of 1 part of a 2% by weight Astrablau solution and 5 parts of a 2% by weight Pyronin solution. The pH of the combined stain was about 2 and one drop of the above stain was mixed with two drops of urine and thereafter subjected to microscopic examination. All of the various constituents of the urine specimen set forth above were visible with the casts being distinct from the cellular material and the nuclear material being distinct from the cytoplasmic material.

EXAMPLE XVII

EXAMPLE I was repeated using a combination of 1 part of a 2% by weight Astrablau solution and 4 parts of a 2% by weight Pyronin solution. The pH of the combined stain was about 2.4 and one drop of the above stain was mixed with two drops of urine and thereafter subjected to microscopic examination. All of the various constituents of the urine specimen set forth above were visible with the casts being distinct from the cellular material and the nuclear material being distinct from the cytoplasmic material.

EXAMPLE XVIII

EXAMPLE I was repeated using a combination of 1 part of a 2% by weight Astrablau solution and 3 parts of a 2% by weight Pyronin solution. The pH of the combined stain was about 2.8 and one drop of the above stain was mixed with two drops of urine and thereafter subjected to microscopic examination. All of the various constituents of the urine specimen set forth above were visible with the casts being distinct from the cellular material and the nuclear material being distinct from the cytoplasmic material.

EXAMPLE XIX

EXAMPLE I was repeated using a combination of 1 part of a 2% by weight Astrablau solution with 2 parts of a 2% by weight Pyronin solution. The pH of the combined stain was about 3.2 and one drop of the above stain was mixed with two drops of urine and thereafter subjected to microscopic examination. All of the various constituents of the urine specimen set forth above were visible with the casts being distinct from the cellular material and the nuclear material being distinct from the cytoplasmic material.

Summarizing, there has been provided a stain for unfixed, wet urinary sediment and cellular elements of serous effusions in which the ratio by weight between the copper phthalocyanin dye to the red xanthene dye is in the range of from about 5 to 1, to about 1 to 5. The pH of the combined dyes in aqueous solution is from about 2 to about 5 with all of the various combinations of dyes disclosed in the 19 specific examples set forth herein being effective to distinctly stain casts from the cellular nuclear material from the cellular cytoplasmic material.

While there has been described what is at present considered to be the preferred embodiment of the present invention, it will be understood that various modifications and alterations may be made herein without departing from the true spirit and scope of the present invention, and it is intended to cover in the appended claims all such modifications and alterations as fall within the true spirit and scope of the present invention.

What is claimed is:

1. A stain for unfixed, wet urinary sediment and cellular elements of serous effusions comprising an aqueous solution having a ph of from about 2 to about 5 including in combination a copper phthalocyanin dye, and a red xanthene dye, wherein the ratio by weight of the copper phthalocyanin dye to the red xanthene dye is in the range of from about 5 to 1 to about 1 to 5, whereby the copper phthalocyanin dye stains the nucleus of damaged cells present in the sediment or serous effusions a blue color and the red xanthene dye stains the cytoplasm of the cells present in the sediment or serous effusions a red color and the mucoproteins present in the sediment or serous effusions are distinctly stained blue to permit differentiation between cellular nuclear material and cellular cytoplasmic material and mucoprotein material.

2. The stain of claim 1, wherein the red xanthene dye is pyronin B.

3. The stain of claim 1, wherein the red xanthene dye is rhodamine 6G.

4. The stain of claim 1, wherein the red xanthene dye is acridene red.

5. The stain of claim 1, wherein the aqueous solution has a ph in the range of from about 2 to about 3.

* * * * *

UNITED STATES PATENT OFFICE
CERTIFICATE OF CORRECTION

Patent No. 3,961,039　　　　　　　Dated June 1, 1976

Inventor(s) Richard Sternheimer

It is certified that error appears in the above-identified patent and that said Letters Patent are hereby corrected as shown below:

Column 1, line 53, after "the" first occurrence insert -- staining --.

Signed and Sealed this

Fifth Day of October 1976

[SEAL]

Attest:

RUTH C. MASON
*Attesting Officer*

C. MARSHALL DANN
*Commissioner of Patents and Trademarks*